(12) United States Patent
Fan et al.

(10) Patent No.: US 7,747,402 B2
(45) Date of Patent: Jun. 29, 2010

(54) METHOD, SYSTEM AND SOFTWARE APPLICATION FOR ELECTROCHEMICAL ANALYSIS

(75) Inventors: Der-Min Fan, Fremont, CA (US); Raymond Gordon White, Saratoga, CA (US); Walter Douglas Modic, Gilroy, CA (US); Henry Hon-Kit Yeung, Cupertino, CA (US); Ronald Steven Baron, San Jose, CA (US); Damon R. Gragg, Livermore, CA (US)

(73) Assignee: Dionex Corporation, Sunnyvale, CA (US)

( * ) Notice: Subject to any disclaimer, the term of this patent is extended or adjusted under 35 U.S.C. 154(b) by 900 days.

(21) Appl. No.: 11/056,839

(22) Filed: Feb. 11, 2005

(65) Prior Publication Data

US 2006/0180478 A1 Aug. 17, 2006

(51) Int. Cl.
*G01R 13/00* (2006.01)
(52) U.S. Cl. .................................................. 702/67
(58) Field of Classification Search .................... 702/23, 702/27, 30, 64, 66, 67, 179; 205/775, 118; 600/365

See application file for complete search history.

(56) References Cited

U.S. PATENT DOCUMENTS

| | | | | |
|---|---|---|---|---|
| 5,374,892 A | * | 12/1994 | Sturrock et al. | 205/775 |
| 5,650,061 A | | 7/1997 | Kuhr et al. | |
| 7,276,029 B2 | * | 10/2007 | Goode et al. | 600/365 |
| 2002/0100692 A1 | * | 8/2002 | Warren et al. | 205/118 |
| 2004/0146909 A1 | * | 7/2004 | Duong et al. | 435/6 |

OTHER PUBLICATIONS

Office Action dated Mar. 24, 2009, received in the European Patent Application which corresponds to U.S. Appl. No. 11/056,839.
EDAQ, "EChem software (ES260)," available at http://www.edaq.com/datasheets/software/ES260.pdf (pub'd online 2003, retrieved May 10, 2006).
Gamry Instruments, "PHE200™ physical electrochemistry software," available at http://www.gamry.com/Sales/Lit_PDF_Files/PHE200.pdf (pub'd online May 15, 2003, retrieved May 10, 2006).
HEKA, "Potmaster manual: multi-channel data acquisition software," available at http://www.heka.com/Download/Manuals/m_potmaster.pdf (pub'd online Sep. 7, 2005; retrieved May 10, 2006).

(Continued)

*Primary Examiner*—Mohamed Charioui
(74) *Attorney, Agent, or Firm*—Morgan, Lewis & Bockius LLP

(57) ABSTRACT

Electrochemical analysis is performed by applying one or more time-sequenced voltage waveforms in a solution and measuring the resulting current in the solution. Raw data representative of the measured current parameters may be integrated based on one or more integration time intervals, and the raw data may be displayed in one or more three dimensional plots. The integrated data and the raw data may also be displayed in one or more two-dimensional plots. The raw data is stored for three dimensional displays and the integrated data is stored for two dimensional displays. Baseline correction is performed on the raw data and the baseline corrected data is displayed in one or more three dimensional plots and in one or more two dimensional plots. The raw data is stored at a rate between 100 Hz and 10 KHz.

37 Claims, 8 Drawing Sheets

OTHER PUBLICATIONS

Kounaves, S., et al., "Acquisition, processing, and presentation of 3-D chromatovoltammographic data using an IBM PS/2 and PAR model 273 potentiostat," *Computers Chem.* 16(1):29-33 (Jan. 1992).

Kounaves, S., et al., "Carbon fiber electrode cell for square wave voltammetric detection of biogenic amines in high-performance liquid chromatography," *Anal. Chem.* 61(13):1469-1472 (1989).

Omanović, D., et al., "Automation of voltammetric measurements by polarographic analyzer PAR 384B," *Croatica Chem. Acta* 71(2):421-433 91998), Dec. 16, 1997.

Princeton Applied Research, "PARSTAT® 2273: Advanced potentiostat/galvanostat/FRA," pp. 1-8, available at http://www.new.ametek.com/content-manager/files/par/2273.pdf (pub'd online Nov. 24, 2004; retrieved May 10, 2006).

* cited by examiner

METHOD, SYSTEM AND SOFTWARE APPLICATION FOR ELECTROCHEMICAL ANALYSIS

TECHNICAL FIELD

The invention relates generally to electrochemical analysis of a solution and more specifically to a method, system and software application for analysis of electrochemical properties of analytes in a sample solution using a measured current as a function of an applied voltage.

BACKGROUND OF THE INVENTION

Several electrochemical methods have been developed to determine the chemical properties of a solution. Common methods are cyclic voltammetry, DC amperometry and integrated amperometry.

Cyclic voltammetry (CV) is a qualitative technique for characterizing the electrochemical properties of compounds in a solution. In CV, a sample solution is subjected to a voltage that is gradually increased and decreased. The resulting current in the solution is measured and is plotted as a function of the applied voltage. From the plot, i.e., the CV plot, electrochemical properties of the solution can be determined, such as, for example, the voltages at which solutes or analytes begin to react and the rates at which they react. The electrochemical properties determined from the CV plot can be used to optimize potentials, i.e., voltages, and measurement times for other electrochemical methods, such as amperometric methods. CV can be used with any type of electrode materials, however it is less sensitive than some other electrochemical methods such as integrated amperometry or DC amperometry.

In DC amperometry, a constant voltage is applied to a sample solution, and the resulting current is measured. When used with carbon electrodes (e.g., glassy carbon, carbon paste, graphite), DC amperometry can be very useful for analysis of organic molecules such as, for example, phenols and catecholamines. DC amperometry is also used with silver electrodes for detection of inorganic ions such as, for example, iodide and cyanide. DC amperometry is not suitable for use with some electrode materials such as platinum and gold. When DC amperometry is used with platinum or gold electrodes, the reaction products from the sample solution remain adsorbed on the electrodes and block the ability of the electrodes to further react with new electrochemically active molecules in the sample solution, resulting in a rapid deterioration of detection response.

Integrated amperometry solves the problem of blocking reaction products by using a rapidly repeating series of potentials (i.e., voltage waveforms) during the electrochemical analysis. After a detection potential is briefly applied, a stronger potential is applied that cleans the reaction products from the electrodes. Thus, integrated amperometry is performed by applying at least two potentials, a detection potential for the purpose of measuring the resulting current and performing analysis and a second potential for the purpose of removing the reaction products from the electrodes. Additional potentials are sometimes used for further cleaning and reconditioning the electrodes and for enhancing adsorption of analytes before the detection potential is again applied. Integrated amperometry is widely used for carbohydrates, amino acids and other mostly organic molecules. Also, integrated amperometry is used in the detection of inorganic anions with silver electrodes.

In integrated amperometry, an electrochemical detector applies a specific voltage waveform to the sample solution through electrodes causing a reaction in the solution. The reaction causes a current to flow in the solution, and the current is measured to determine the solution's chemical properties. Since different compounds undergo reactions at different applied voltages and with different kinetics, the optimum waveform for use varies from compound to compound.

Until now, the capabilities of electrochemical methods have been limited by the limitations of the electrochemical detectors. Existing electrochemical detectors generally do not provide multiple waveforms in a single injection to analyze different analytes in a sample solution to increase analysis throughput. Also, the existing electrochemical detectors do not allow a wide range of potentials in a waveform in a single injection so that an optimal integration interval for each analyte in the solution can be selected. Some electrochemical detectors have attempted to overcome these limitations by using multiple electrodes, but this approach is expensive. Furthermore, the existing electrochemical detectors perform data analysis at the hardware level, so raw data was not available for further analysis. Important details in raw data can be lost if data analysis settings are not optimal, and because hardware settings can only be changed prior to analysis, such details can only be found by running multiple experiments using different settings.

Accordingly, there is a need for a method, system and a software application that generates multiple waveforms to analyze different analytes in a solution to increase analysis throughput. There is also a need for a method, system and software application that provides optimized detection of multiple analytes in the solution. There is also a need for a method, system and software application that transfers raw data to a software application that can perform post-run data analysis and integration. There is also a need for a method and system that generates three dimensional and real time plots from data derived from CV, DC amperometry, and integrated amperometry.

SUMMARY OF THE INVENTION

The invention is directed to a method, system and software application for electrochemical analysis of analytes in a solution. The invention stores raw data set received from an electrochemical analysis and analyzes and displays the analyzed data and the raw data. The electrochemical analysis is performed by applying one or more time-sequenced voltage waveforms in the solution and measuring the resulting current in the solution. In one aspect, the method comprises receiving raw data from the electrochemical analysis wherein the raw data is representative of the measured current parameters. The raw data may be integrated based on one or more integration time intervals, and the raw data may be displayed in one or more three dimensional plots. The integrated data and the raw data may also be displayed in one or more two-dimensional plots.

The method further includes storing the raw data for three dimensional displays and storing the integrated data for two dimensional displays. The method further includes performing baseline correction of the raw data and displaying the baseline corrected data in one or more three dimensional plots and in one or more two dimensional plots. The method further includes performing arithmetic operations on the raw data and the integrated data. The raw data is transmitted and stored at a rate between 100 Hz and 10 KHz. In one embodiment, the data is transmitted at 1 KHz. The invention can be utilized in integrated amperometry, DC amperometry, cyclic voltammetry or other types of electrochemical analysis techniques.

DETAILED DESCRIPTION OF PREFERRED EMBODIMENTS

In one embodiment, the invention is directed to a method, system and software application for measuring chemical properties and concentration of compounds in a solution using electrochemical or electoanalytical methods (i.e., chromatogram). The method, system and software application processes data generated by an electrochemical or electroanalytical detection process such as integrated amperometry, DC amperometry and cyclic voltammetry. In the following description, the terms "electrochemical" and "electroanalytical" are used interchangeably, and the terms "software application" and "computer program product" are used interchangeably.

In one embodiment of the invention, an electrochemical detection system includes a plurality of working electrodes and reference electrodes. The electrochemical detection system applies one or more voltage waveforms through the working electrodes to the solution. The system allows an operator to select the parameters of the waveform(s) such as the type of waveform (e.g., square wave, triangular wave, pulse wave, etc), the magnitude of the waveform, and the period of the waveform. In response to the applied voltage, a current is produced in the solution. The working electrodes measure the current in the solution and the reference electrodes provide a reference for the working electrode to drive a voltage waveform. The electrochemical detection system generates high speed data representative of the measured current. In one embodiment, the system generates data at a rate preferably between 100 Hz and 10 KHz. In one embodiment, the system generates 1 KHz data. The software application receives the 1 KHz data and analyzes the data to determine the chemical properties and concentration of the chemicals in the solution.

Unlike conventional electrochemical detection systems, the system does not require hardware integrators and signal processing circuits to analyze the data. Rather, the data (e.g., 1 KHz data) representative of the measured current is provided to the software application. The software application analyzes the data, which is displayed in two-dimensional and three-dimensional plots. In one embodiment, data from DC amperometry and cyclic voltammetry is displayed in two-dimensional plots and data from integrated amperometry is displayed in three-dimensional plots. In the following descriptions, the terms "plot" and "display" are used interchangeably, and thus the terms "two dimensional plots" and "three dimensional plots" are used interchangeably with "two dimensional displays" and "three dimensional displays", respectively.

Figure 1:
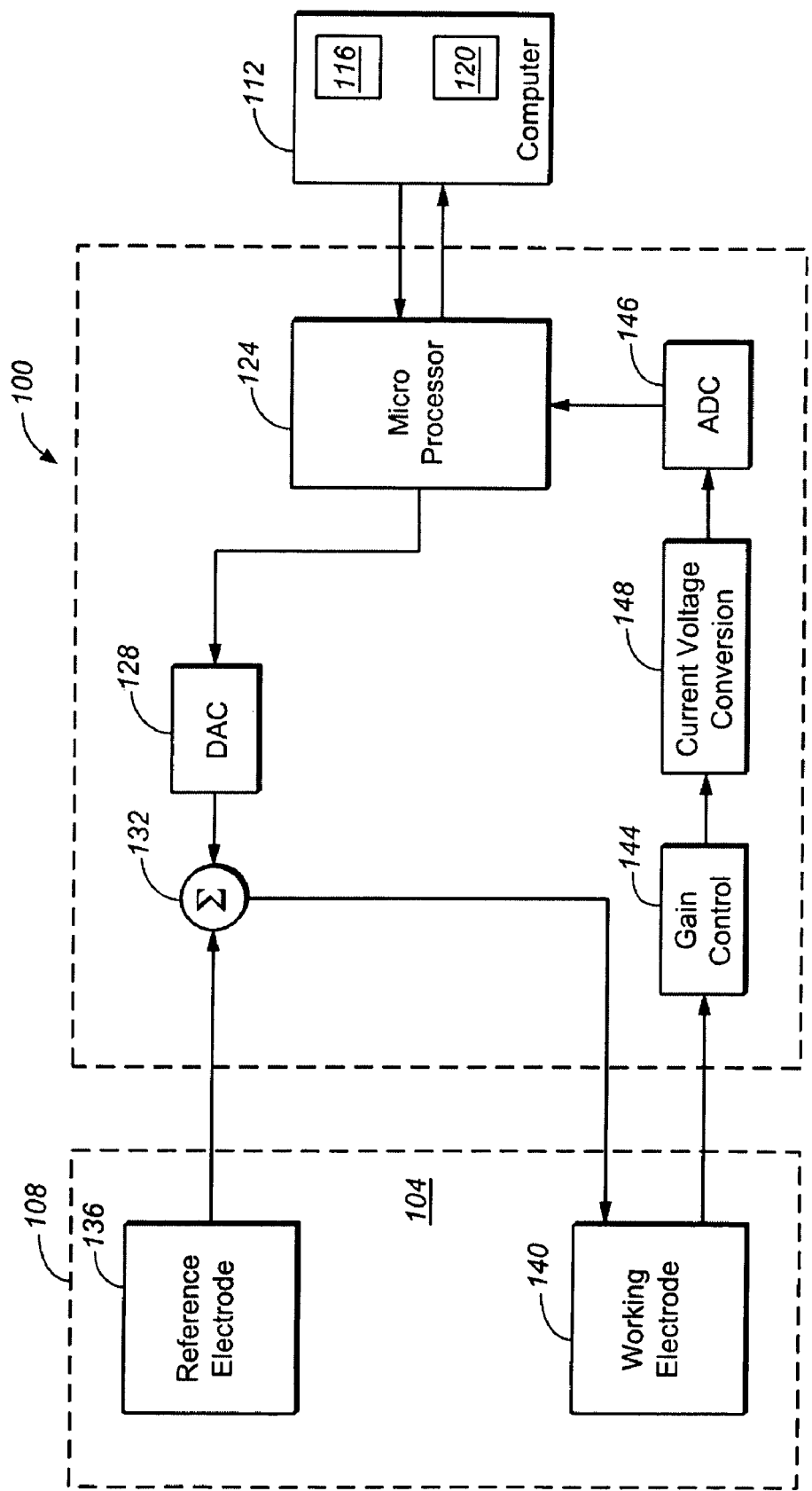
FIG. 1 illustrates an electrochemical detection system in accordance with one embodiment of the present invention.

FIG. 1 shows an electrochemical detection system 100 in accordance with one embodiment of the present invention. The detection system 100 is designed to perform electrochemical analysis or chromatogram on solution 104 in an electrochemical cell 108 to determine the chemical properties and concentration of various compounds in the solution. The solution 104 may include one or more analytes. In the following description, the terms solution and analyte(s) is used interchangeably.

The detection system 100 is controlled by a computer 112. The computer 112 may be a personal computer that provides a user interface with the detection system 100. The computer 112 includes a graphics display 116 that permits an operator to observe the progress of an experiment. The graphics display 116 indicates response of the solution or analyte(s) to the applied voltage waveforms, thus enabling the operator to see the experiment results.

A software application 120 resides in the computer 112. As discussed before, the software application 120 is configured to analyze the data and to generate one or more plots representative of the data. The features and advantages of the software application will be discussed later.

The detection system 100 includes a microprocessor 124 configured to generate one or more voltage waveforms responsive to commands from the computer 112. An operator using the computer 112 may control the parameters of the voltage waveforms generated by the microprocessor 124. For example, the operator can direct the microprocessor to generate a sawtooth wave having period of 500 ms. The microprocessor 124 can also generate other types of waveforms such as, for example, triangular waves, pulse waves, DC, etc. The microprocessor 124 also relays data collected by the detection system 100 for analysis by the computer 112. The data from the microprocessor 124 to the computer 112 may use any of a multitude of different communication mechanisms, either packetized or streaming. In addition to the data, the corresponding waveform voltage value, synchronization flags indicating the start of each successive waveform, flags indicating that the waveform has changed, and gain range values (if using an auto-ranging ADC circuit) can all be included by the microprocessor 124 in the data stream to allow proper storage and processing of the data by the computer 112.

The detection system 100 includes a digital to analog converter (DAC) 128. The DAC 128 receives a digital signal (i.e., data) representative of the waveform generated by the microprocessor 124 and converts the digital signal to an analog signal. The analog signal is received by a summing circuit 132.

The electrochemical cell 108 includes reference electrodes 136 and working electrodes 140. The reference electrodes 136 are used to monitor the cell voltage in the analyte(s) 104. The working electrodes 140 are used to apply the voltage to the analyte(s) and also to measure the current produced in the analyte(s).

The summing circuit 132 receives the reference voltage from the reference electrodes 136. The reference voltage is a dc bias signal that is added to the analog signal (generated by the DAC 128). The sum of the reference voltage and the analog signal is designated as the "applied voltage waveform" that is applied into the analyte(s) through the working electrodes 140.

In response to the applied voltage waveform, a chemical reaction occurs in the analytes(s) causing a flow of an electrical current. The electrical current is measured by the working electrodes 140 and the measured current signal is provided to a gain control circuit 144. The gain control circuit 144 adjusts the gain of the measured current signal and provides the adjusted current signal to a current to voltage converter 148 in real time. The current to voltage converter 148 converts the adjusted current signal to a voltage signal. The voltage signal is received by an analog to digital converter (ADC) 146 that converts the voltage signal to a digital signal (i.e., data) representative of the voltage signal. The microprocessor 124 can apply any necessary calibration and conversion operations to the data needed to convert it into the proper units for the host computer 112. The microprocessor will interact with the gain control circuit 144 and the ADC 146 in order to derive the proper scaling of the raw data and to remove any discontinuities in the samples as gain ranges change. The data is provided to the host computer 112 via the microprocessor 124. Thus, the electrochemical detection system 100 measures the current in the analyte(s) 104 in response to an applied voltage. The detection system 100 converts the measured current to raw data representative of the measured current and provides the raw data to the host computer 112 for further analysis.

In one embodiment, the detection system 100 generates data at a rate between 100 Hz and 10 KHz. In one embodiment, the detection system 100 generates data at 1 KHz rate. The detection system 100 includes a buffer that stores a predetermined amount of raw data, e.g., data over a 10 second period. The raw data provided by the detection system 100 is also referred to as the high speed data.

The computer 112 includes the software application 120 that stores and analyzes the 1 KHz raw data. In one embodiment, the software application 120 includes a data buffer. The data buffer is configured to store raw data for one or more waveform cycles.

In one embodiment, the raw data and the applied voltage are stored in a format that includes various parameters of the raw data and the applied voltage for 3-dimensional data display.

In one embodiment, the software application stores raw data in waveform cycles. Each cycle of data has information about the raw data and an autozero value. For example, a voltage waveform having a period of 500 ms is applied to the analyte(s) for a run time of 5 minutes in an integrated amperometry analysis. Such an experiment would generate 600 waveform cycles (5*60/0.5). The software application will acquire (600*500) or 300000 data points corresponding to the measured currents and autozero values from the hardware. As will be understood by those skilled in the art, the autozero value allows the display of the total signal or the offset signal.

Figure 2A:
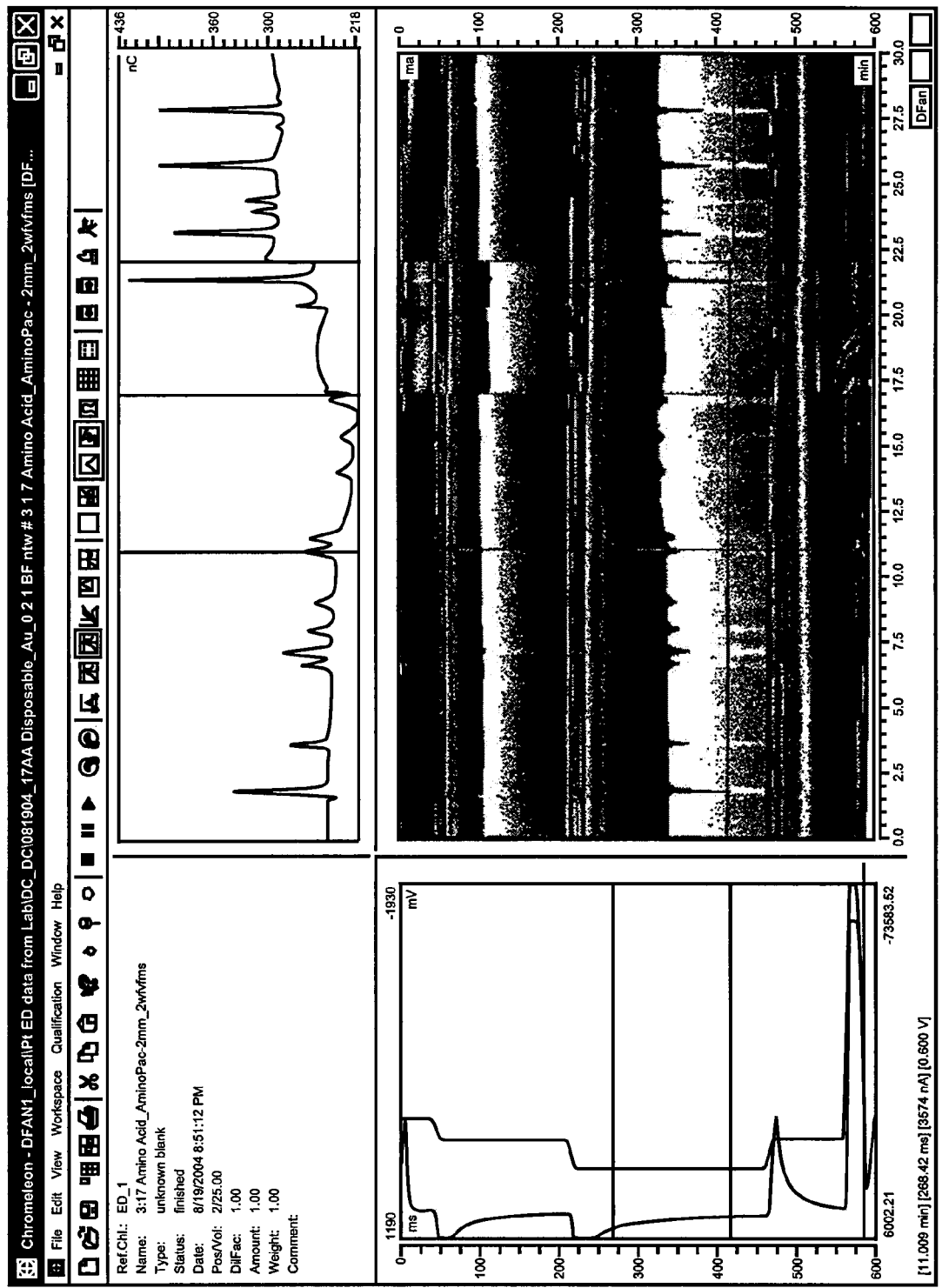
FIG. 2a illustrates three dimensional iso-plot of raw data.

The software application 120 displays the raw data representative of the measured current as a three-dimensional plot. The three-dimensional plot displays the magnitude of the measured current, the time interval of the measurement, and the waveform cycles included in the raw data. In FIG. 2a, the bottom right frame illustrates a three-dimensional plot displaying the raw data acquired from an integrated amperometry. In FIG. 2a, the vertical lines represent raw data from a waveform cycle. The magnitude of the measured current is indicated by the pixel color. The horizontal axis represents the time interval of the experiment. Thus, the three-dimensional plot illustrates the time interval of the experiment, the duration of waveforms used in the experiments, and the measured currents. The raw 3-D amperometry data can be displayed as an isometric plot as shown in the lower right frame of FIG. 2a.

Figure 2B:
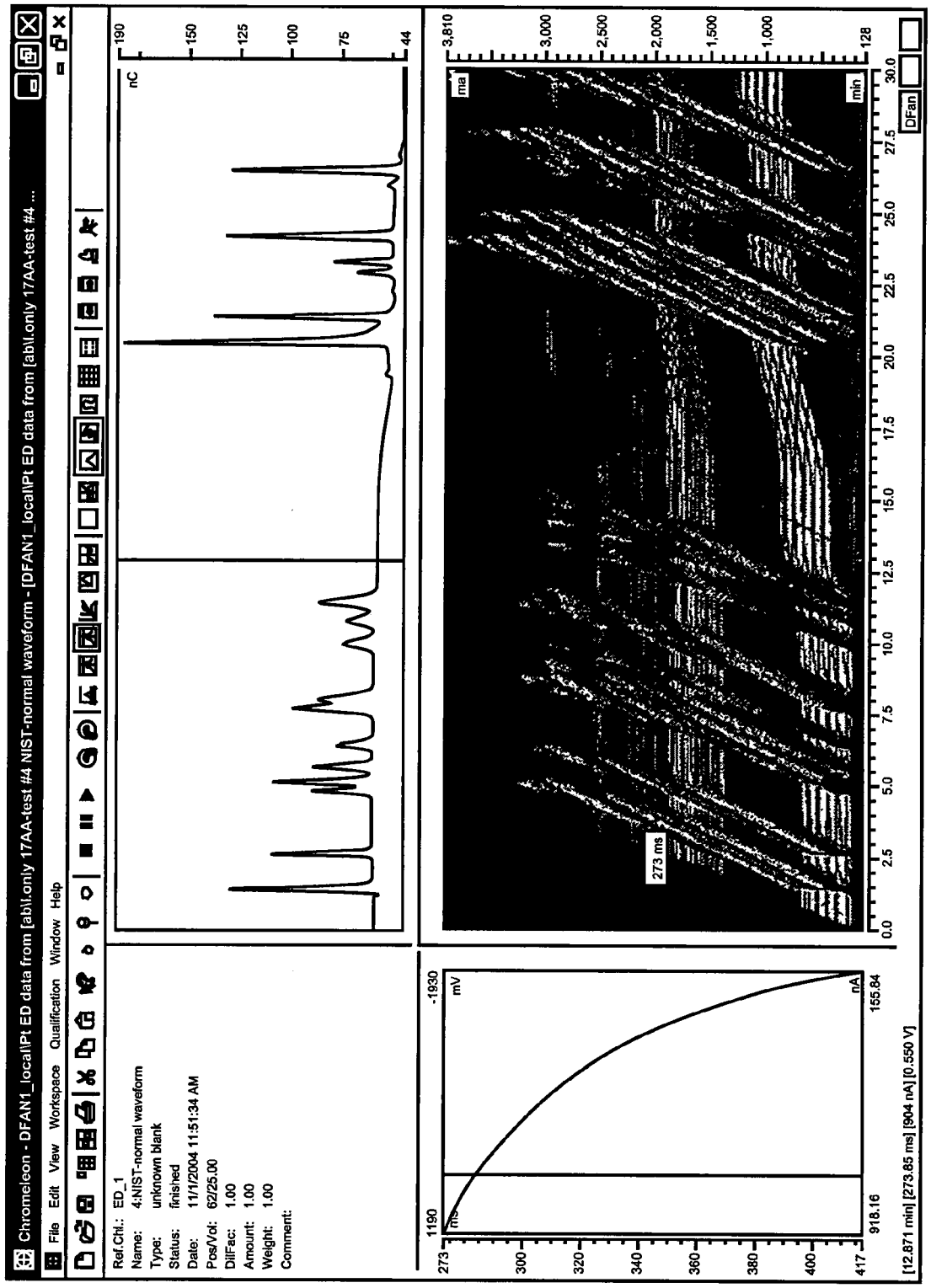
FIG. 2b illustrates three dimensional wire frame contour plots of raw data.

The raw 3-D amperometry data can also be displayed as a wire frame contour plot as shown in the lower right frame of FIG. 2b.

The software application also displays raw data of a particular waveform cycle in a two dimensional plot. In FIG. 2a, the lower left frame illustrates a two-dimensional plot of the raw data displaying the magnitude of the measured current, the applied voltage waveform, and the time of the waveform.

The software application also displays a chromatogram in a two dimensional plot as shown in the upper right frame in FIG. 2a. The chromatogram plot can be generated either by retrieving one raw data point per waveform from the selected 3D data or by calculating one integrated data point per waveform from the selected 3D data. The horizontal axis is the time interval of the experiment and the vertically axis is the current response. The current response can be represented in nano amps (nA) units for raw data or nano columns (nC) units for integrated data. The upper left frame in FIG. 2a provides information about the sample solution.

If integration is enabled, parallel horizontal lines on the 3-D plot shown in the lower right frame of FIG. 2a and the I-t plot (i.e., current versus time plot) shown in the lower left frame of FIG. 2a are used to select the integration interval. The integration interval can be moved by dragging the top line on either the 3D (i.e., three-dimensional) or I-t (i.e., current versus time) plot. The integration interval can be increased or decreased by dragging the bottom line. When the integration interval is changed, new data is integrated, creating a new chromatogram that is displayed on a chromatogram plot.

If the integration is disabled, a single horizontal line on the three-dimensional plot shown in the lower right frame in FIG. 2a and the I-t plot (i.e., current versus time) shown in the lower left frame of FIG. 2a is used to select a waveform time slice. The selected waveform time determines which data points are used to plot the chromatogram. The horizontal line can be moved to select a different waveform time and to generate a new chromatogram.

The movable vertical line on the 3-D plot shown in the lower right frame of FIG. 2a and the chromatogram plot shown in the upper right frame of FIG. 2a is used to select a retention time. The selected retention time determines which data points are used to create the I-t plot. The line can be moved to select a different retention time and thus generate a corresponding I-t plot.

The mouse can be used to zoom into an area of a plot. By drawing a frame around an area (clicking and dragging), the area can be zoomed.

If multiple waveforms are applied during a test run (i.e., experiment), or if additional integration intervals are added post-run, non-movable vertical markers are used to designate where each waveform or integration change occurs.

Figure 3:
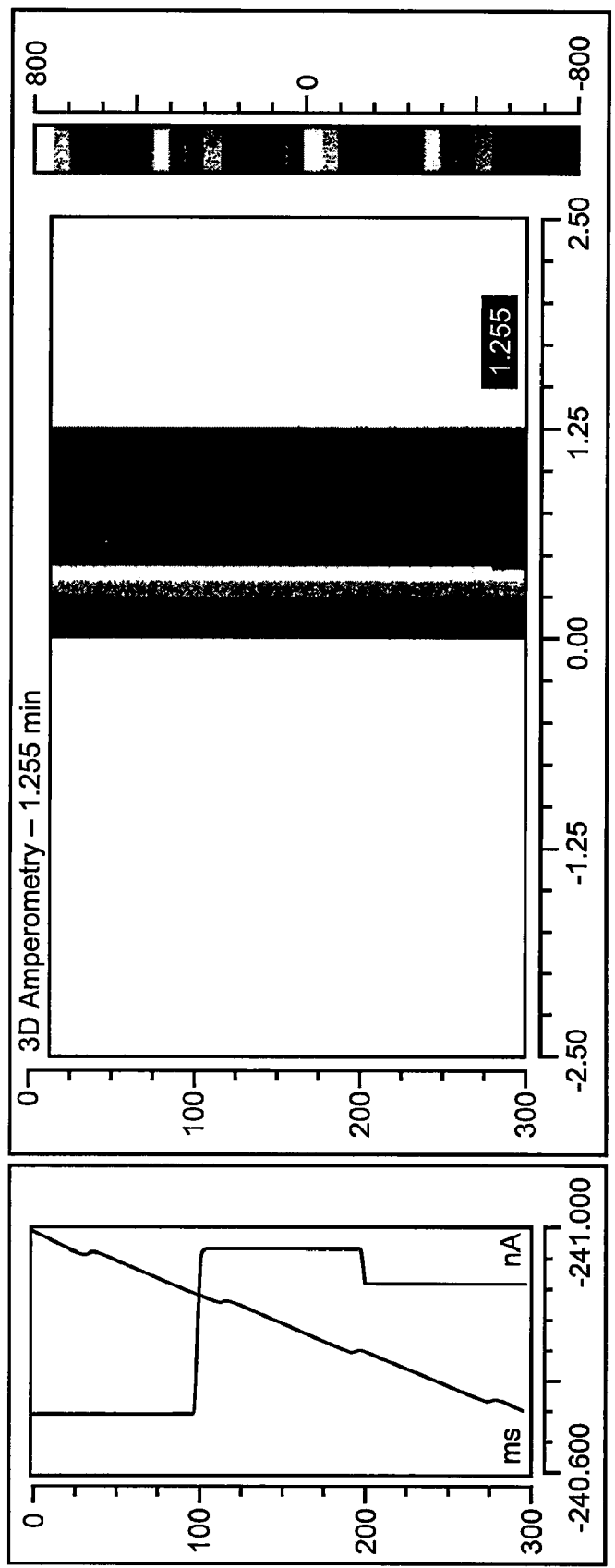
FIG. 3 illustrates a real-time two-dimensional plot of an applied voltage waveform and resulting current.

FIG. 3 illustrates the real time plots of an integrated amperometry. The left frame in FIG. 3 shows a step voltage (the applied waveform) and the resulting measured current. The right frame in FIG. 3 shows a three-dimensional plot of the raw data.

In one embodiment, the raw data is integrated by the software application 120 and the integrated data is displayed in a two-dimensional plot. In FIGS. 2a and 2b the top right frame illustrates results of an integrated data in a two-dimensional plot. The horizontal axis represents run time and the vertical axis represents magnitude (nanoColumbs).

In one embodiment, the software application generates one integrated data or data value for each waveform cycle. One integrated data value for one cycle of raw data corresponds to the total amount of charges detected between the time period t1 and t2 within the waveform period, where t1 and t2 are the user defined integration interval. In one embodiment, the duration of each data point is 1 millisecond, and the charges of each data point is its measured current multiplied by 0.001 second. The summation of the charges for all data points between t1 and t2 is the integrated data. For example, if the detection system 100 generates 1 KHz data (i.e., 100 data points) between the time intervals t1=100 ms and t2=200 ms, and if the total value of the 100 data points is 355444.78 nA, the integrated value is 355.44 nC.

Without the raw data, the software application must rely on the integrated data generated by hardware to perform the calculation. With raw data saved by the software, it can be retrieved and re-integrated to generate an optimal Integrated Amperometry chromatogram.

In one embodiment, the software application allows an operator to change one or more integration intervals to display different integrated data after the data acquisition. Referring back to the integration example provided earlier, the operator may change the integration interval to t1=120 ms and t2=235 ms. The software application will integrate the 1 KHz data from 120 ms to 235 ms. The integrated data can be displayed in a two-dimensional plot.

Referring back to FIG. 2a, the operator can move the horizontal line in the lower right frame to change the integration interval interactively, and the result of the integrated data will be immediately displayed in the top right frame. The operator may extract integrated data or raw data and display the extracted data as a two-dimensional plot as shown in FIG. 2a.

The plot in the lower left frame in FIG. 2a is driven by the vertical line in the three-dimensional plot in the lower right frame in FIG. 2a.

The software application provides multiple channels to display data. For example, a plurality of channels can be used to display a plurality of sets of data. Thus, an operator may display a first set of data in a first two-dimensional channel, a second set of data in second two-dimensional channel, and a third set of data in a first three-dimensional channel. The software application allows an operator to perform various arithmetic operations on raw data and integrated data. For example, the operator may combine two or more channels of two dimensional data and display the combined data on a new channel. The results of the arithmetic combinations can be displayed in one or more plots.

Figure 4:
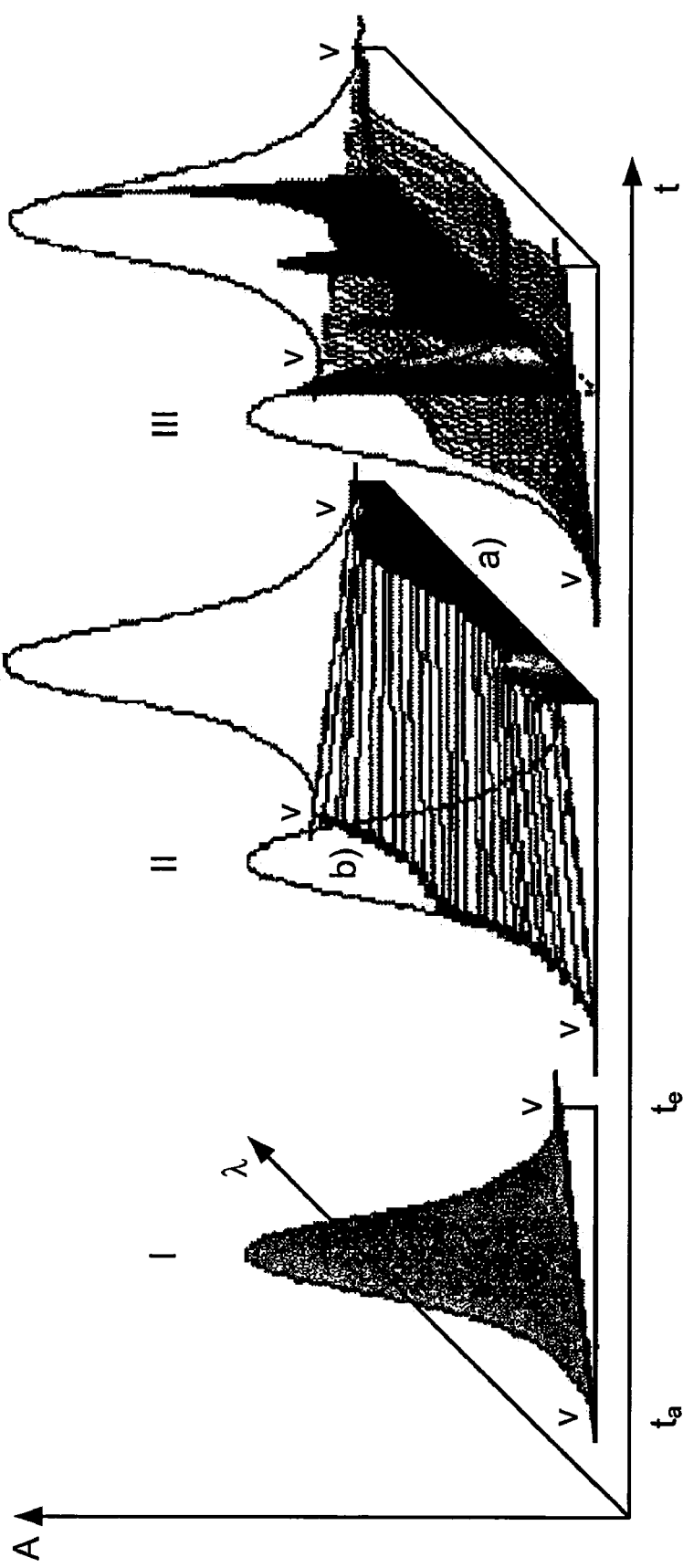
FIG. 4 illustrates the baseline correction process.

The software application provides baseline correction of data. The baseline correction of an I-t curve (i.e., current versus time) allows an operator to compare a plurality of I-t curves under different conditions. The baseline correction allows peak I-t curves on a gradient or I-t curves of Rider Peaks to be represented more precisely because a large "underground portion" caused by the gradient portion or the large main peak is considered. The application establishes the start and end of the peaks for a given 'reference' channel and marks the start and end of the peaks by positioning two peak delimiters, ta and te. The baseline (I) is then drawn between the two delimiters, ta and te. The steps are repeated every millisecond for a waveform. The response, i.e., current values, at each millisecond of a waveform is measured between the time periods ta and te, and a baseline I-t curve is generated with peak start and peak end. The application interpolates the curves and calculates a separate baseline response for each data point of a peak. FIG. 4 illustrates the baseline correction process.

Figure 5A:
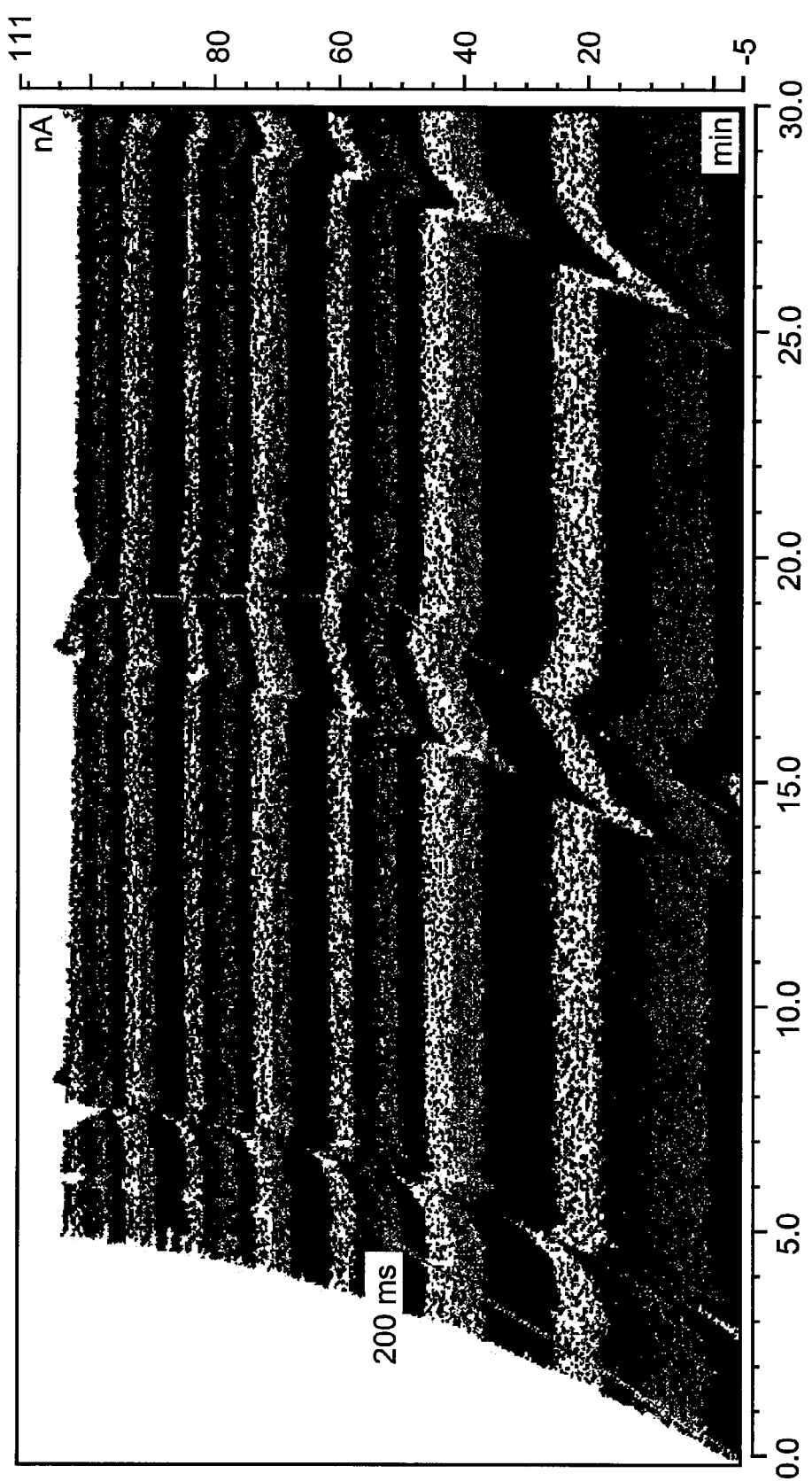
FIGS. 5a-5b illustrate examples of generating baseline corrected current plots from measured currents.
Figure 5B:
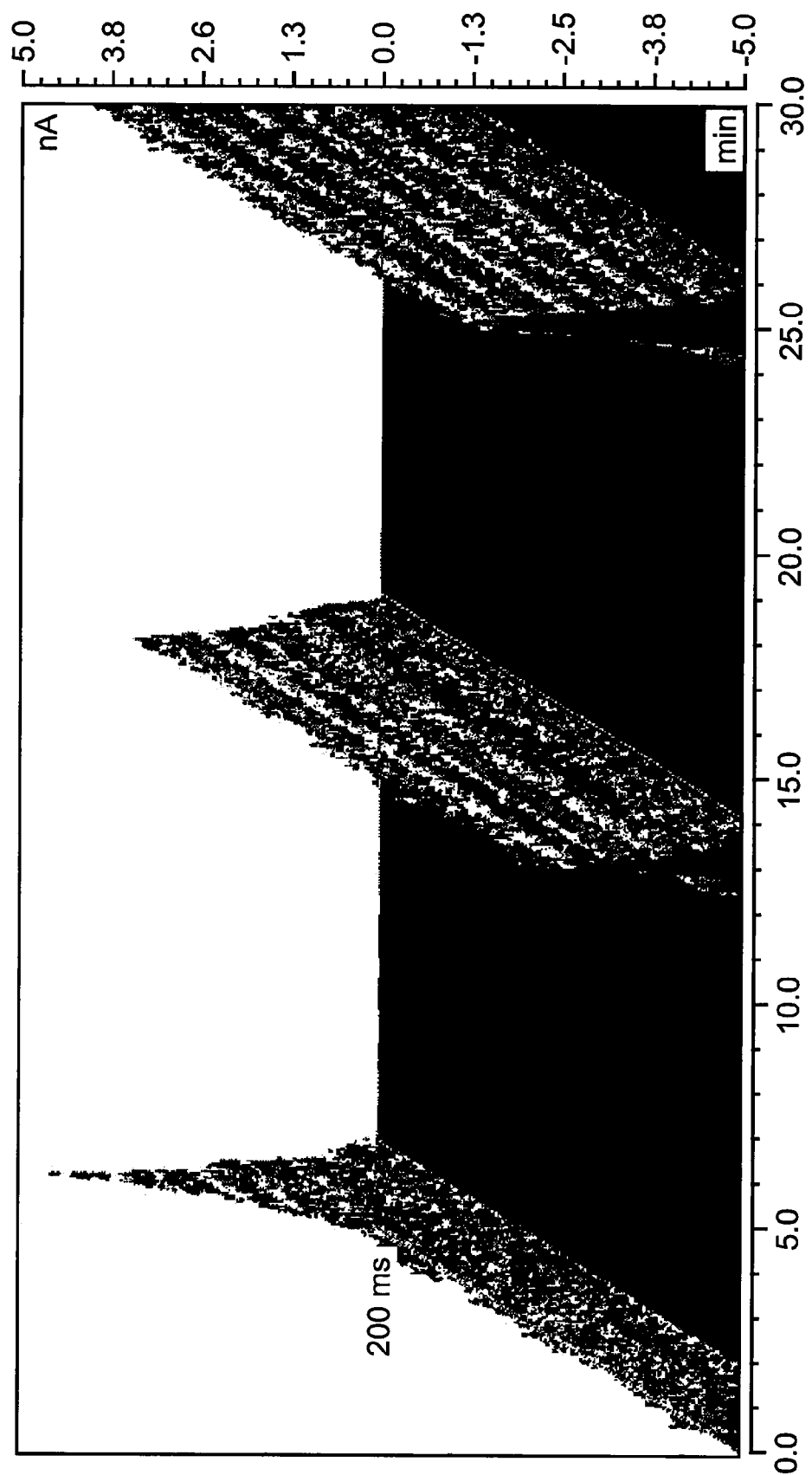

FIGS. 5a and 5b illustrate a example of generating baseline corrected plots from measured currents and backgrounds. FIG. 5a illustrates a a three-dimensional plot of measured current. FIG. 5b is a baseline corrected plot. The benefits of baseline correction can be easily seen in FIG. 5b, where peak symmetry is restored by removing the gradient elements. The application also allows baseline correction with manual re-integration. An operator may manually shift peak delimiters. After each manual shift, new baseline I-t curves are automatically re-interpolated and re-calculated.

Figure 6:
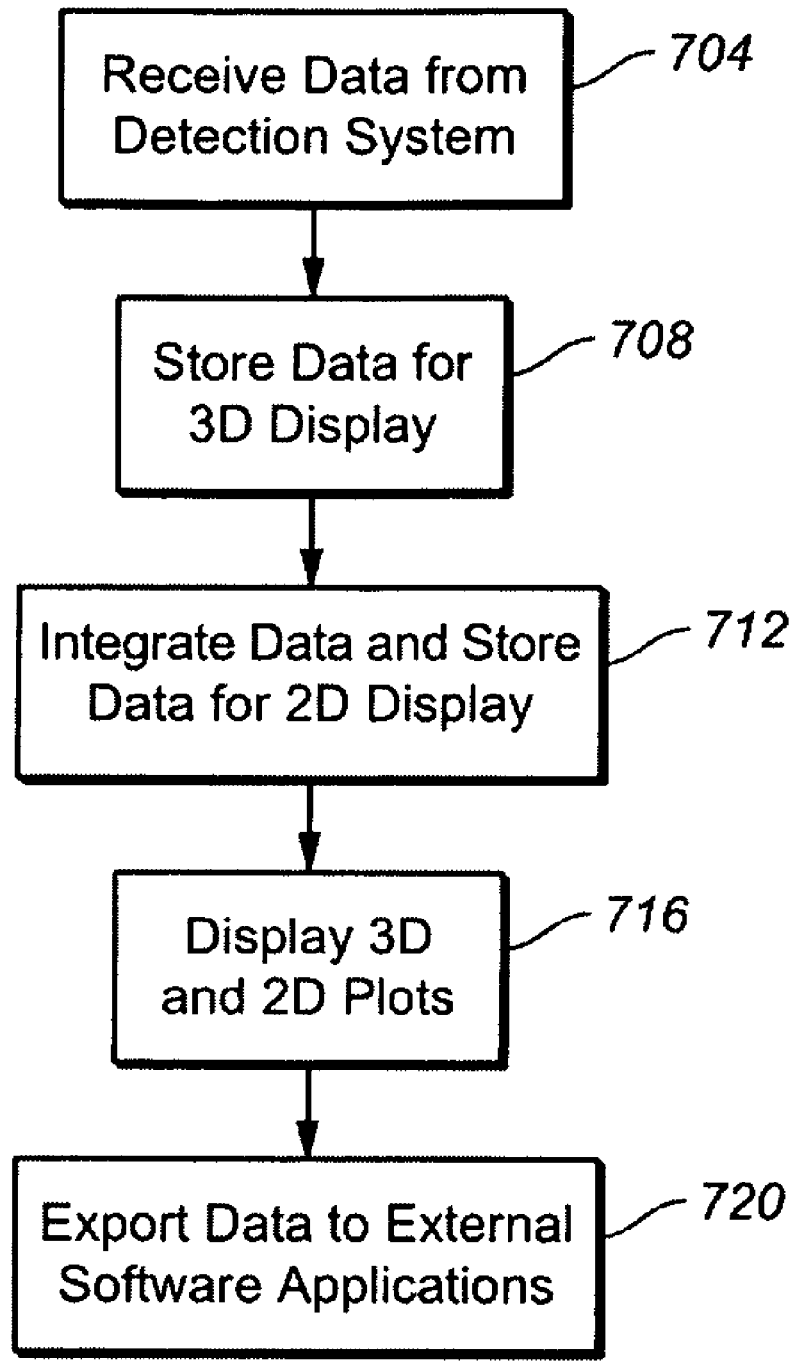
FIG. 6 is a flow diagram of the method steps for receiving and displaying measured data from an electrochemical analysis in accordance with one embodiment of the invention.

FIG. 6 is a flow diagram of the method steps for receiving and displaying measured data from an electrochemical analysis in accordance with one embodiment of the invention. In step 704, the software application receives the data (also referred to as raw data) generated by an electrochemical detection system. In one embodiment, the software application receives 1 KHz data. In step 708, the raw data is stored for three-dimensional display. In step 712, the data is integrated and stored for two-dimensional display. In step 716, the raw data, the integrated data, and the applied voltage waveform are displayed in various plots. In step 720, the data is exported to an external software application.

In one embodiment of the invention, the software application is embodied in a computer program product such as a compact disk, a hard drive, a floppy disk, a magnetic tape drive or any other memory device. The computer program product includes computer readable program code for executing method steps for analyzing the chemical properties of analyte(s) and displaying the results of the analysis.

It is to be understood that even though various embodiments and advantages of the present invention have been set forth in the foregoing description, the above disclosure is illustrative only, and changes may be made in detail, and yet remain within the broad principles of the invention. For example, although the software application has been described in connection with the detection system 100, it will be understood by those skilled in the art that the software application may be adapted for use in other types of detection systems and in connection with various electrochemical or electroanalytical techniques. Therefore, the present invention is to be limited only by the appended claims.

What is claimed is:

1. A computer-implemented method for analyzing and displaying data comprising:
   at a computer,
     first, receiving raw data from electrochemical analysis performed by a separate test device by applying one or more voltage waveforms on analyte(s), wherein the raw data is representative of current parameters measured in the analyte(s);
     second, storing the received raw data;
     third, receiving one or more user-selected processing parameters;
     fourth, processing the raw data based on the one or more user-selected processing parameters to produce processed data, wherein the raw data that is processed includes portions of the raw data received prior to the selection by the user of the processing parameters; and
     fifth, providing a response based on the processed data.

2. The method of claim 1, further comprising: at the computer,
   receiving a user-defined adjustment to at least one of the user-selected processing parameters;
   processing the raw data based on the user-defined adjustment; and
   providing an adjusted response based on the processing.

3. The method of claim 2, wherein the one or more user-selected processing parameters include one or more integration time intervals, and wherein processing the raw data includes integrating the raw data based on the one or more integration time intervals to generate integrated data.

4. The method of claim 3, further comprising performing arithmetic operations on the integrated data.

5. The method of claim 3, wherein providing a response based on the processing includes:
displaying a magnitude of the integrated data as a function of time in a two-dimensional plot.

6. The computer-implemented method of claim 1, further comprising:
displaying the raw data in a first plot as a function of time; and
wherein receiving one or more user-selected processing parameters comprises receiving a user's selection of a portion of the first plot.

7. The computer-implemented method of claim 6, wherein providing a response comprises displaying processed data in a second plot while simultaneously displaying the first plot.

8. The method of claim 1, further comprising performing baseline correction of the raw data, and displaying the baseline corrected data in a three dimensional display.

9. The method of claim 1, wherein one or more processing parameters include one or more arithmetic operations, and wherein processing the raw data includes performing the one or more arithmetic operations on the raw data.

10. The method of claim 1, further comprising:
displaying the raw data in at least one three-dimensional plot as a function of a time interval of the electrochemical analysis and a duration of the application of the one or more voltage waveforms.

11. The method of claim 1, further comprising:
displaying the raw data of a first waveform of the one or more voltage waveforms in at least one two-dimensional plot as a function of a duration of the application of the first waveform.

12. A computer readable storage medium having one or more programs configured for execution by a computer, the one or more programs comprising instructions for:
first, receiving raw data from electrochemical analysis performed by a separate test device by applying one or more voltage waveforms on analyte(s), wherein the raw data is representative of current parameters measured in the analyte(s);
second, storing the received raw data;
third, receiving one or more user-selected processing parameters;
fourth, processing the raw data based on the one or more user-selected processing parameters to produce processed data, wherein the raw data that is processed includes portions of the raw data received prior to the selection by the user of the processing parameters; and
fifth, generating a response based on the processed data.

13. The computer readable medium of claim 12, further including instructions for:
receiving a user-defined adjustment to at least one of the user-selected processing parameters;
processing the raw data based on the user-defined adjustment; and
generating an adjusted response based on the processing of the raw data.

14. The computer readable medium of claim 13, wherein the one or more processing parameters include one or more integration time intervals, and wherein processing the raw data includes integrating the raw data based on the one or more integration time intervals to generate integrated data.

15. The computer readable medium of claim 14, further comprising instructions for performing arithmetic operations on the integrated data.

16. The computer readable medium of claim 14, further comprising instructions for receiving a user-defined adjustment to the one or more integration time intervals, and in response, modifying the one or more integration time intervals.

17. The computer readable medium of claim 14, further comprising instructions for re-integrating the raw data with different integration parameters to provide the adjusted response.

18. The computer readable medium of claim 14, wherein instructions for providing a response based on the processing include:
instructions for displaying a magnitude of the integrated data as a function of time in a two-dimensional plot.

19. The computer readable storage medium of claim 12, further comprising: instructions for displaying the raw data in a first plot as a function of time; and
wherein instructions for receiving one or more user-selected processing parameters comprises instructions for receiving a user's selection of a portion of the first plot.

20. The computer readable storage medium of claim 19, further comprising:
instructions for providing a response comprises instructions for displaying processed data in a second plot while simultaneously displaying the first plot.

21. The computer readable medium of claim 12, further comprising instructions for performing baseline correction of the raw data, and for displaying the baseline corrected data in three dimensional plots and two dimensional plots.

22. The computer readable medium of claim 12, wherein one or more processing parameters include one or more arithmetic operations, and wherein processing the raw data includes performing the one or more arithmetic operations on the raw data.

23. The computer readable medium of claim 12, further including instructions for:
displaying the raw data in at least one three-dimensional plot as a function of a time interval of the electrochemical analysis and a duration of the application of the one or more voltage waveforms.

24. The computer readable medium of claim 12, further including instructions for:
displaying the raw data of a first waveform of the one or more voltage waveforms in at least one two-dimensional plot as a function of a duration of the application of the first waveform.

25. A system comprising:
a processor circuit configured to generate at least one digital voltage waveform;
a first converter circuit configured to receive the digital voltage waveform and responsively to generate an analog voltage waveform;
at least one first electrode configured to receive the analog voltage waveform and responsively to apply the analog voltage waveform to analyte(s) and to measure the resulting current signal in the analyte(s);
a second converter circuit configured to receive the measured current signal and responsively to generate raw data representative of the measured current signal;
a computer having an associated computer-readable storage medium to store one or more programs configured for execution by a computer, the one or more programs comprising instructions for:

first, receiving the raw data;

second, storing the received raw data;

third, receiving one or more user-selected processing parameters;

fourth, processing the raw data based on the one or more user-selected processing parameters to produce processed data, wherein the raw data that is processed includes portions of the raw data received prior to the selection by the user of the processing parameters; and fifth, providing a response based on the processed data.

26. The system of claim 25, further including instructions for:

receiving a user-defined adjustment to at least one of the user-selected processing parameters;

processing the raw data based on the user-defined adjustment; and providing an adjusted response based on the processing.

27. The system of claim 26, wherein the one or more user selected processing parameters include one or more integration time intervals, and wherein processing the raw data includes integrating the raw data based on the one or more integration time intervals to generate integrated data.

28. The system of claim 27, wherein instructions for providing a response based on the processing include:

instructions for displaying the integrated data and the raw data in at least one two-dimensional plot.

29. The system of claim 27, wherein instructions for providing a response based on the processing include:

instructions for displaying a magnitude of the integrated data as a function of time in a two-dimensional plot.

30. The system of claim 26, further comprising:

a user interface operable to receive the one or more user-selected processing parameters and the user-defined adjustment.

31. The system claim 26, further comprising instructions for:

performing baseline correction of the raw data, and displaying the baseline corrected data in a three dimensional display.

32. The system claim 25, further comprising:

instructions for displaying the raw data in a first plot as a function of time; and wherein instructions for receiving one or more user-selected processing parameters comprises instructions for receiving a user's selection of a portion of the first plot.

33. The system of claim 32, further comprising:

instructions for providing a response comprises instructions for displaying processed data in a second plot while simultaneously displaying the first plot.

34. The system of claim 25, further comprising a summing circuit coupled to the first converter circuit and adapted to receive the reference voltage and the analog voltage waveform and responsive to generate a resultant voltage waveform, and wherein the resultant voltage waveform is applied to the analytes.

35. The system of claim 25, wherein one or more user selected processing parameters include one or more arithmetic operations, and wherein processing the raw data includes performing the one or more arithmetic operations on the raw data.

36. The system of claim 25, further including instructions for:

displaying the raw data in at least one three-dimensional plot as a function of a time interval of the electrochemical analysis and a duration of the application of the one or more voltage waveforms.

37. The system of claim 25, further including instructions for:

displaying the raw data of a first waveform of the one or more voltage waveforms in at least one two-dimensional plot as a function of a duration of the application of the first waveform.

* * * * *